United States Patent
Sohier et al.

(10) Patent No.: US 7,226,612 B2
(45) Date of Patent: Jun. 5, 2007

(54) COATING FOR MEDICAL DEVICES

(75) Inventors: Jerome Sohier, Zeist (NL); Jeroen Mattijs Bezemer, Utrecht (NL)

(73) Assignee: Chienna B.V., Bilthoven (NL)

( * ) Notice: Subject to any disclaimer, the term of this patent is extended or adjusted under 35 U.S.C. 154(b) by 236 days.

(21) Appl. No.: 10/673,041

(22) Filed: Sep. 25, 2003

(65) Prior Publication Data

US 2005/0101692 A1 May 12, 2005

Related U.S. Application Data

(63) Continuation of application No. PCT/NL02/00212, filed on Apr. 2, 2002.

(30) Foreign Application Priority Data

Apr. 4, 2001 (EP) .................................. 01201259

(51) Int. Cl.
*A61F 2/62* (2006.01)
*A61F 2/00* (2006.01)
*C08L 67/00* (2006.01)

(52) U.S. Cl. .................. 424/426; 524/17; 524/601; 427/2.1

(58) Field of Classification Search ............... 524/17, 524/601; 424/426; 427/2.1; 428/480
See application file for complete search history.

(56) References Cited

U.S. PATENT DOCUMENTS

| 3,908,201 A | | 9/1975 | Jones et al. ............... 3/1 |
| 5,480,436 A | * | 1/1996 | Bakker et al. ............. 600/37 |
| 5,980,948 A | * | 11/1999 | Goedemoed et al. ....... 424/489 |
| 6,280,457 B1 | * | 8/2001 | Wallace et al. ............. 606/200 |
| 6,656,489 B1 | * | 12/2003 | Mahmood et al. .......... 424/426 |
| 6,685,957 B1 | * | 2/2004 | Bezemer et al. ............. 424/426 |
| 2002/0095213 A1 | * | 7/2002 | Bakker et al. ........... 623/13.11 |
| 2003/0199969 A1 | * | 10/2003 | Steinke et al. ............. 623/1.16 |
| 2003/0206928 A1 | * | 11/2003 | Tormala et al. ............. 424/400 |

FOREIGN PATENT DOCUMENTS

| EP | 0 830 859 | 3/1998 |
| EP | 1 002 859 | 5/2000 |
| WO | WO 01/10478 | 2/2001 |
| WO | WO 02/060508 | 8/2002 |

\* cited by examiner

*Primary Examiner*—Tae H Yoon
(74) *Attorney, Agent, or Firm*—Banner & Witcoff, Ltd.

(57) ABSTRACT

The invention relates to a coating for medical devices. The coating comprises a specific copolymer of which the composition may be adjusted such as to achieve an excellent adhesion to a wide range of surfaces. The coating may further comprise an additive, such as a biologically active agent, which may be released in vivo in a controlled manner, as the degradability of the coating may also be adjusted to a predetermined rate. The invention further relates to a process for applying the coating to a surface and to a medical device comprising the coating.

21 Claims, 2 Drawing Sheets

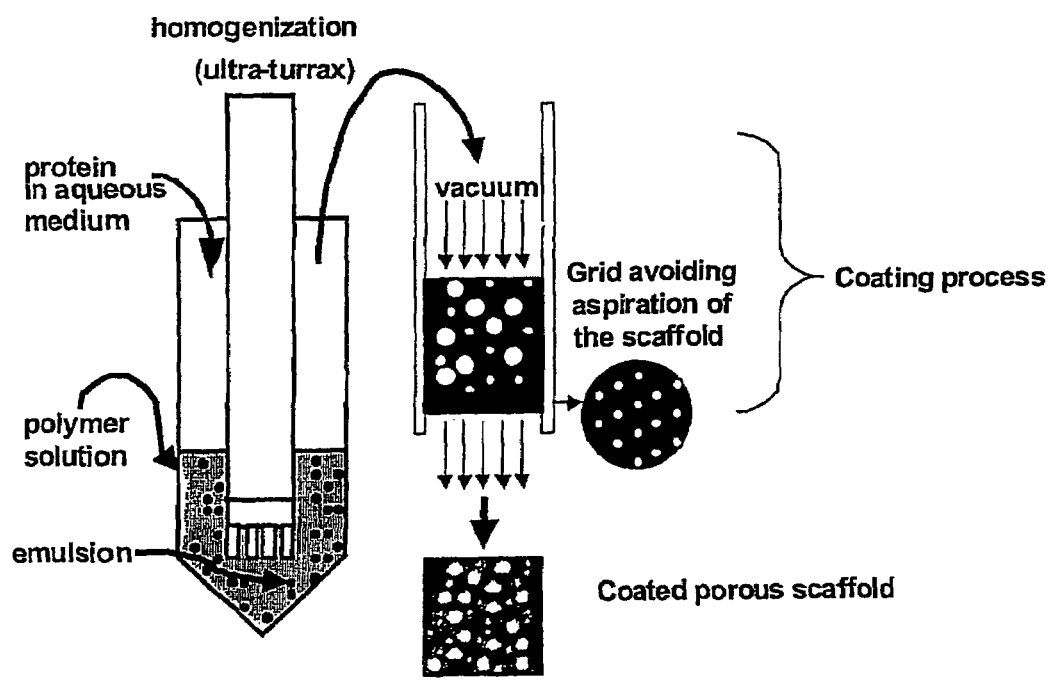
Figure 1: Principle of coating of a porous scaffold using an protein containing emulsion.

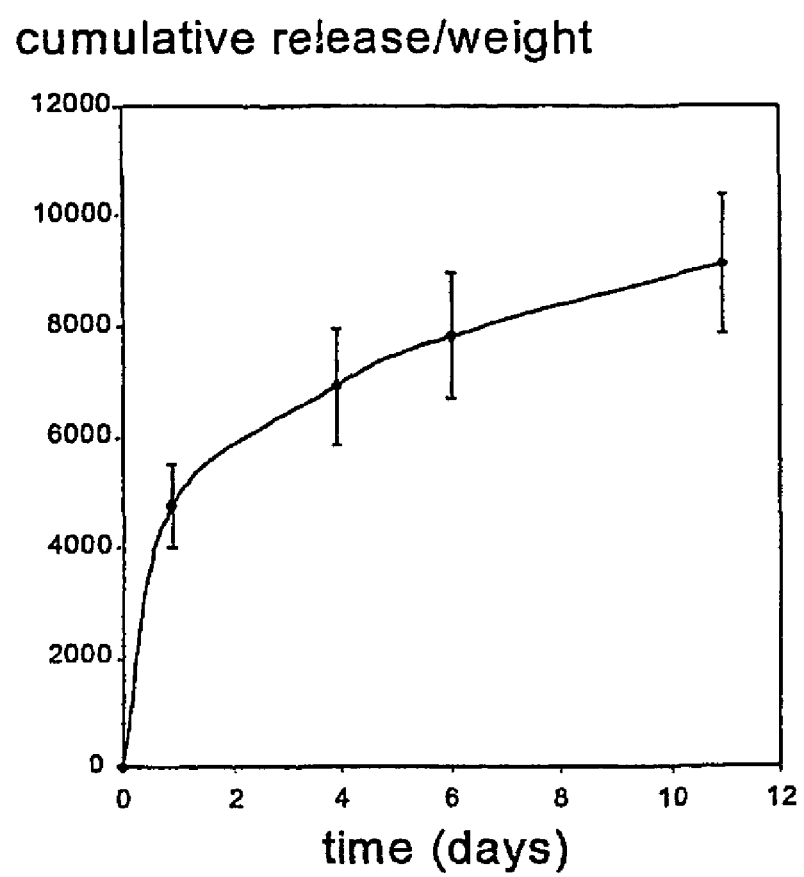
Figure 2: Release of lysozyme from coated scaffolds

COATING FOR MEDICAL DEVICES

This application is a continuation of International Patent Application Ser. No. PCT/NL02/00212, filed Apr. 2, 2002; which claims priority from European patent application number 01201259.7, filed Apr. 4, 2001; both of which are hereby incorporated herein by reference.

BACKGROUND

The invention relates to a coating for medical devices. The invention further relates to a process for applying a coating to a surface, e.g. a surface of a medical device, and to a medical device comprising said coating.

Great effort has been put into studies of coatings for medical devices. Materials used for the manufacture of medical devices are not always chosen from a biocompatability point of view as often other considerations, e.g. with respect to strength or tensile and stretching properties, prevail.

Coatings for medical devices are, however, not only interesting for enhancing the biocompatibility of a medical device. They also provide a possibility to provide a controlled release of biologically active agents, in which case it is necessary that the coating is also biodegradable.

Problems encountered in the design of coatings for medical devices are many. One of the bigger problems concerns the adhesion of the coating to the material of which the medical device is made. As many different materials, varying from metals to ceramics and polymeric materials, are used for the manufacture of medical devices, it is important that a good coating adheres sufficiently to all sorts of materials. This is, however, often not the case.

Another problem concerns the conditions a medical device is subjected to during use. Certain medical devices, such as catheters, are for instance subjected to deformation in vivo. When the device expands, it is important that the coating is capable of undergoing the same deformation without breaking or coming loose. This would lead to exposure of the surface of the material of the medical device to the surrounding tissue in vivo. In the worst case, parts of the coating might detach from the device completely.

Accordingly, there is a need for a coating material for medical devices which may be used universally for different sorts of medical devices of different materials.

SUMMARY

The invention provides a coating that fulfils this need. A specific copolymer has been found of which the properties may be adjusted to the needs and requirements of application on a specific medical device of a specific material. Accordingly, the invention relates to a coating for a medical device comprising a copolymer of a polyalkylene glycol terephtalate and an aromatic polyester.

A coating according to the invention may be applied to a wide range of materials. It is one of the great advantages of the invention that the composition of the copolymer may be adjusted such as to achieve a good adhesion to nearly any type of material. The nature and molecular weights of the monomers of the copolymer, as well as the ratio of the two monomers and the molecular weight of the copolymer itself, provide a multitude of variations that can be used to achieve an optimum property profile of a coating. These parameters do not only serve to adjust the adhesion of the coating. Other properties can be optimised as well. Examples of such properties include the degradability and swelling behaviour of the coating and mechanical properties, like elasticity and tensile strength. Other properties and advantages will become clear form the following, more detailed description of the invention.

A coating according to the invention comprises a copolymer of a polyalkylene glycol terephtalate and an aromatic polyester. Preferably, the copolymer comprises 20–90 wt. %, more preferably 40–70 wt. % of the polyalkylene glycol terephtalate, and 80–10 wt. %, more preferably 60–30 wt. % of the aromatic polyester. A preferred type of copolymers according to the invention is formed by the group of block copolymers.

The polyalkylene glycol may have a weight average molecular weight of about 150 to about 10000. Preferably, the polyalkylene glycol has a weight average molecular weight of 200 to 4000. The aromatic polyester preferably has a weight average molecular weight of from 200 to 9000, more preferably from 250 to 4000. The weight average molecular weight of the copolymer preferably lies between 10,000 and 300,000, more preferably between 40,000 and 120,000.

BRIEF DESCRIPTION OF THE DRAWINGS

FIG. 1 depicts a schematic representation of coating a porous scaffold using a protein-containing emulsion.

FIG. 2 graphically depicts the release of lysozyme from coated scaffolds.

DETAILED DESCRIPTION OF CERTAIN PREFERRED EMBODIMENTS

The weight average molecular weight may suitably be determined by gel permeation chromatography (GPC). This technique, which is known per se, may for instance be performed using chloroform, hexafluoro isopropanol or m-cresol as a solvent and polystyrene as external standard. Alternatively, a measure for the weight average molecular weight may be obtained by using viscometry (see NEN-EN-ISO 1628-1). This technique may for instance be performed at 25° C. using chloroform as a solvent. Preferably, the intrinsic viscosity of the copolymer lies between 0.2 and 1.5 dL/g, which corresponds to a weight average molecular weight between 10,000 and 300,000. Likewise, the more preferred ranges for the weight average molecular weight measured by GPC mentioned above can also be expressed in terms of the intrinsic viscosity.

In a preferred embodiment, the polyalkylene glycol terephtalate component has units of the formula —OLO—CO-Q-CO—, wherein O represents oxygen, C represents carbon, L is a divalent organic radical remaining after removal of terminal hydroxyl groups from a poly(oxyalkylene)glycol, and Q is a divalent organic radical.

Preferred polyalkylene glycol terephtalates are chosen from the group of polyethylene glycol terephtalate, polypropylene glycol terephtalate, and polybutylene glycol terephtalate and copolymers thereof, such as poloxamers. A highly preferred polyalkylene glycol terephtalate is polyethylene glycol terephtalate.

The terms alkylene and polyalkylene generally refer to any isomeric structure, i.e. propylene comprises both 1,2-propylene and 1,3-propylene, butylene comprises 1,2-butylene, 1,3-butylene, 2,3-butylene, 1,2-isobutylene, 1,3-isobutylene and 1,4-isobutylene (tetramethylene) and similarly for higher alkylene homologues. The polyalkylene glycol terephtalate component is preferably terminated with a dicarboxylic acid residue —CO-Q-CO—, if necessary to provide a coupling to the polyester component. Group Q may be an aromatic group having the same definition as R, or may be an aliphatic group such as ethylene, propylene, butylene and the like.

The polyester component preferably has units —O-E-O—CO—R—CO—, wherein O represents oxygen, C represents carbon, E is a substituted or unsubstituted alkylene or oxydialkylene radical having from 2 to 8 carbon atoms, and R is a substituted or unsubstituted divalent aromatic radical.

In a preferred embodiment, the polyester is chosen from the group of polyethylene terephthalate, polypropylene terephthalate, and polybutylene terephthalate. A highly preferred polyester is polybutylene terephthalate.

The preparation of the copolymer will now be explained by way of example for a polyethylene glycol terephtalate/polybutylene terephthalate copolymer. Based on this description, the skilled person will be able to prepare any desired copolymer within the above described class. An alternative manner for preparing polyalkylene glycol terephtalate/polyester copolymers is disclosed in U.S. Pat. No. 3,908,201.

A polyethylene glycol terephtalate/polybutylene terephthalate copolymer may be synthesized from a mixture of dimethyl terephtalate, butanediol (in excess), polyethylene glycol, an antioxidant and a catalyst. The mixture is placed in a reaction vessel and heated to about 180° C., and methanol is distilled as transesterification proceeds. During the transesterification, the ester bond with methyl is replaced with an ester bond with butylene and/or the polyethyene glycol. After transesterification, the temperature is raised slowly to about 245° C., and a vacuum (finally less than 0.1 mbar) is achieved. The excess butanediol is distilled off and a prepolymer of butanediol terephthalate condenses with the polyethylene glycol to form a polyethylene/polybutylene terephthalate copolymer. A terephthalate moiety connects the polyethylene glycol units to the polybutylene terephthalate units of the copolymer and thus such a copolymer also is sometimes referred to as a polyethylene glycol terephtalate/polybutylene terephthalate copolymer (PEGT/PBT copolymer).

In principle, a coating according to the invention of the above described copolymer may be applied to any type of surface. In fact, it is one of the great advantages of the invention that the properties of the copolymer may be adjusted over a wide range so that a good adhesion to all sorts of materials may be achieved. At the same time, the properties of the copolymer may be set such as to provide a certain desired degradability profile in vivo, which enables the use of the coating for controlled release of additives, such as biologically active agents. In addition, depending on the chosen composition of the copolymer, a certain swelling behaviour may be set. Swelling may serve as an additional tool to modulate release of active agents from the coating. When the coating is used on certain types of medical devices, e.g. which are subject to deformation during use in vivo, an elastic behaviour may be very useful.

Examples of materials onto the surface of which a coating according to the invention may be applied include metals and alloys, ceramics, glasses, and polymers. More specific examples of metals include stainless steel, titanium, nickel, cobalt, chrome, niobium, molybdenum, zirconium, tantalum, and combinations thereof. Further, ceramic materials, such as alumina and zirconia, glasses such as bioactive glasses made of $CaO$—$SiO_2$—$P_2O_5$, and calcium phosphates, such as hydroxyapatite and tricalcium phosphate, may be coated in accordance with the invention. The subject coatings can further be applied to various polymers and plastics, more preferably biocompatible or bioresorbable ones like polylactic acid or polyglycolic acid, but also polyolefines, such as (ultra high molecular weight) polyethylene and the like.

The material of which a surface is coated may be a flat, dense or a complex shaped body. It may have a porous, beaded or meshed ingrowth surface, all depending on the purpose of the body.

In a preferred embodiment, the coating is applied to a medical device, which is to be used in vivo. Examples of medical devices that may be coated according to the invention include, but are not limited to, catheters, fibres, nonwoven fabrics, vascular grafts, porous metals for e.g. acetabulum revision, dental filling materials, materials for approximation, adhesion of tissues, materials used in osteosynthesis (e.g. pins or bone screws), cardiac patches, sutures, soft and hard tissue scaffolds and fillers (e.g. collagen, calcium phosphate, bioglass), stents, bone void fillers intended for the repair of bone defects, intrauterine devices, root canal fillers, drug delivery pumps, implantable infusion pumps, spacer devices, implants containing medicinal products, and scaffolds for tissue engineering.

As has been mentioned, the composition of the copolymer of which a coating according to the invention is made, may be adjusted to provide optimal properties for adhesion on various surfaces. In addition the composition may be adjusted to achieve predetermined other properties, such as swelling behaviour and biodegradability. This adjusting may be done as follows.

It envisaged that, under certain circumstances, two coatings are applied. For instance, in case the coating is to be applied to an inert surface (like a metal or metal alloy surface), a first coating of the copolymer having a relatively hydrophobic character, and a second coating of the copolymer having a different, less hydrophobic character, are applied. The first hydrophobic coating may serve to promote adhesion to the substrate, whereas the second coating may assist in or be responsible for release of a biologically active agent.

The rate of degradation of the coating may be set by the weight percentage poly(ethylene glycol) terephtalate in the copolymer. A higher relative amount of PEGT will generally result in a faster degradation.

The swelling behaviour of the coating can be influenced by the length of the poly(ethylene glycol) terephtalate segments and/or the weight percentage poly(ethylene glycol) terephtalate in the copolymer. A higher amount of PEGT, or, more important, longer PEGT segments, will generally increase the tendency of the coating to swell, as well as the extent of swelling.

The above mentioned additives that can be incorporated into the coating may vary widely in nature; in principle any type of additive may be incorporated as long as its nature or used amount does not obstruct with the coating-forming capacity of the copolymer. Depending on the envisaged application of the surface onto which the coating of the copolymer is applied, the additive may be chosen from the group of biologically active agents. As the copolymer is biodegradable in vivo, and allows diffusion of molecules, the additives will be released to the surroundings of the coating in a controlled manner. This behaviour of the copolymer has previously been described in EP-A-0 830 859. These additives may be added to the solution in amounts ranging from 0 to 50 wt. %, preferably from 1 to 20 wt. %.

The term "biologically active agent", as used herein, means an agent which provides a therapeutic or prophylactic effect. Such agents include, but are not limited to, antimicrobial agents (including antibacterial and anti-fungal agents), anti-viral agents, anti-tumor agents, hormones immunogenic agents, growth factors, lipids, and lipopolysaccharides.

Biologically active agents which may be incorporated include, but are not limited to, non-peptide, non-protein small-sized drugs. They have a molecular weight which in general is less than 1500, and in particular less than 500. A second important group of biologically active agents are biologically active peptides and proteins.

Examples of non-peptide, non-protein small-sized drugs which may be incorporated include, but are not limited to, the following:
1. Anti-tumor agents: altretamin, fluorouracil, amsacrin, hydroxycarbamide, asparaginase, ifosfamid, bleomycin, lomustin, busulfan, melphalan, chlorambucil, mercaptopurin, chlormethin, methotrexate, cisplatin, mitomycin, cyclophosphamide, procarbazin, cytarabin, teniposid, dacarbazin, thiotepa, dactinomycin, tioguanin, daunorubicin, treosulphan, doxorubicin, tiophosphamide, estramucin, vinblastine, etoglucide, vincristine, etoposid, vindesin.
2. Antimicrobial Agents
   2.1 Antibiotics
   Penicillins: ampicillin, nafcillin, amoxicillin, oxacillin, azlocillin, penicillin G, carbenicillin, penicillin V, dicloxacillin, phenethicillin,
   floxacillin, piperacillin, mecillinam, sulbenicilin, methicillin, ticarcillin, mezlocillin
   Cephalosporins: cefaclor, cephalothin, cefadroxil, cephapirin, cefamandole, cephradine, cefatrizine, cefsulodine, cefazolin, ceftazidim, ceforanide, ceftriaxon, cefoxitin, cefuroxime, cephacetrile, latamoxef, cephalexin
   Aminoglycosides: amikacin, neomycin, dibekacyn, kanamycin, gentamycin, netilmycin, kanamycin, tobramycin
   Macrolides: amphotericin B, novobiocin, bacitracin, nystatin, clindamycin, polymyxins, colistin, rovamycin, erythromycin, spectinomycin, lincomycin, vancomycin
   Tetracyclines: chlortetracycline, oxytetracycline, demeclocycline, rolitetracycline, doxycycline, tetracycline, minocycline
   Other antibiotics: chloramphenicol, rifamycin, rifampicin, thiamphenicol
   2.2 Chemotherapeutic Agents
   Sulfonamides: sulfadiazine, sulfamethizol, sulfadimethoxin, sulfamethoxazole, sulfadimidin, sulfamethoxypyridazine, sulfafurazole, sulfaphenazol, sulfalene, sulfisomidin, sulfamerazine, sulfisoxazole, trimethoprim with sulfamethoxazole or sulfametrole
   Urinary tract antiseptics: methanamine, quinolones (norfloxacin, cinoxacin), nalidixic acid, nitro-compounds (nitrofurantoine, nifurtoinol), oxolinic acid
   Anaerobic infections: metronidazole
3. Drugs for tuberculosis: aminosalicyclic acid, isoniazide, cycloserine, rifampicine, ethambutol, tiocarlide, ethionamide, viomycin
4. Drugs for leprosy: amithiozone, rifampicine, clofazimine, sodium sulfoxone, diaminodiphenylsulfone (DDS, dapsone)
5. Antifungal agents: amphotericin B, ketoconazole, clotrimazole, miconazole, econazole, natamycin, flucytosine, nystatine, griseofulvin
6. Antiviral agents: aciclovir, idoxuridine, amantidine, methisazone, cytarabine, vidarabine, ganciclovir
7. Chemotherapy of amebiasis: chloroquine, iodoquinol, clioquinol, metronidazole, dehydroemetine, paromomycin, diloxanide, furoatetinidazole, emetine
8. Anti-malarial agents: chloroquine, pyrimethamine, hydroxychloroquine, quinine, mefloquine, sulfadoxine/pyrimethamine, pentamidine, sodium suramin, primaquine, trimethoprim, proguanil
9. Anti-helminthiasis agents: antimony potassium tartrate, niridazole, antimony sodium dimercaptosuccinate, oxamniquine, bephenium, piperazine, dichlorophen, praziquantel, diethylcarbamazine, pyrantel parmoate, hycanthone, pyrivium pamoate, levamisole, stibophen, mebendazole, tetramisole, metrifonate, thiobendazole, niclosamide
10. Anti-inflammatory agents: acetylsalicyclic acid, mefenamic acid, aclofenac, naproxen, azopropanone, niflumic acid, benzydamine, oxyphenbutazone, diclofenac, piroxicam, fenoprofen, pirprofen, flurbiprofen, sodium salicyclate, ibuprofensulindac, indomethacin, tiaprofenic acid, ketoprofen, tolmetin
11. Anti-gout agents: colchicine, allopurinol
12. Centrally acting (opoid) analgesics: alfentanil, methadone, bezitramide, morphine, buprenorfine, nicomorphine, butorfanol, pentazocine, codeine, pethidine, dextromoramide, piritranide, dextropropoxyphene, sufentanil, fentanyl
13. Local anesthetics: articaine, mepivacaine, bupivacaine, prilocalne, etidocaine, procaine, lidocaine, tetracaine
14. Drugs for Parkinson's disease: amantidine, diphenhydramine, apomorphine, ethopropazine, benztropine mesylate, lergotril, biperiden, levodopa, bromocriptine, lisuride, carbidopa, metixen, chlorphenoxamine, orphenadrine, cycrimine, procyclidine, dexetimide, trihexyphenidyl
15. Centrally active muscle relaxants: baclofen, carisoprodol, chlorinezanone, chlorzoxazone, cyclobenzaprine, dantrolene, diazepam, febarbamate, mefenoxalone, mephenesin, metoxalone, methocarbamol, tolperisone
16. Hormones and hormone antagonistics
    16.1 Corticosteroids
        16.1.1 Mineralocorticosteroids: cortisol, desoxycorticosterone, flurohydrocortisone
        16.1.2 Glucocorticosteroids: beclomethasone, betamethasone, cortisone, dexamethasone, fluocinolone, fluocinonide, fluocortolone, fluorometholone, fluprednisolone, flurandrenolide, halcinonide, hydrocortisone, medrysone, methylprednisolone, paramethasone, prednisolone, prednisone, triamcinolone (acetonide)
    16.2 Androgens
        16.2.1 Androgenic steroids used in therapy: danazole, fluoxymesterone, mesterolone, methyltestosterone, testosterone and salts thereof
        16.2.2 Anabolic steroids used in therapy: calusterone, nandrolone and salts thereof, dromostanolone, oxandrolone, ethylestrenol, oxymetholone, methandriol, stanozolol methandrostenolone, testolactone
        16.2.3 Antiandrogens: cyproterone acetate
    16.3 Estrogens
        16.3.1 Estrogenic steroids used in therapy: diethylstilbestrol, estradiol, estriol, ethinylestradiol, mestranol, quinestrol
        16.3.2 Anti-estrogens: chlorotrianisene, clomiphene, ethamoxytriphetol, nafoxidine, tamoxifen
    16.4 Progestins: allylestrenol, desogestrel, dimethisterone, dydrogesterone, ethinylestrenol, ethisterone, ethynadiol diacetate, etynodiol, hydroxyprogesterone, levonorgestrel, lynestrenol, medroxyprogesterone, megestrol acetate, norethindrone, norethisterone, norethynodrel, norgestrel, progesterone
17. Thyroid drugs
17.1 Thyroid drugs used in therapy: levothyronine, liothyronine
17.2 Anti-thyroid drugs used in therapy: carbimazole, methimazole, methylthiouracil, propylthiouracil When a non-peptide, non-protein, small-sized drug, such as those described above, is to be incorporated, the polyalkylene glycol terephtalate component of the copolymer preferably has a molecular weight of from about 200 to 400. Also, the polyalkylene glycol terephtalate component is present in the copolymer in an amount of from 20 wt. % to 90 wt. % of the weight of the copolymer, preferably from about 40 wt. % to about 70 wt. % of the weight of the copolymer. In general, the aromatic polyester is present in the copolymer in an amount of from 10 wt. % to 80 wt. % of the copolymer, preferably in an amount of from about 30 wt. % to about 60 wt. % of the copolymer.

When a hydrophobic small-sized drug, such as, for example, a steroid hormone is incorporated, preferably at least one hydrophobic antioxidant is present. Hydrophobic antioxidants which may be employed include, but are not limited to, tocopherols, such as α-tocopherol, β-tocopherol, γ-tocopherol, δ-tocopherol, ε-tocopherol, $\xi_1$-tocopherol, $\xi_2$-tocopherol, and η-tocopherol; and 1-ascorbic acid 6-palmitate. Such hydrophobic antioxidants retard the degradation of the copolymer and retard the release of the biologically active agent. Thus, the use of a hydrophobic or lipophilic antioxidant is applicable particularly to the formation of matrices which include drugs which tend to be released quickly from the coating, such as, for example, small drug molecules having a molecular weight less than 500. The at least one hydrophobic antioxidant may be present in the coating in an amount of from about 0.1 wt. % to about 10 wt. % of the total weight of the matrix, preferably from about 0.5 wt. % to about 2 wt. %.

When the coating includes a hydrophilic small-sized drug, such as an aminoglycoside, it may also include, in addition to the hydrophobic antioxidant, a hydrophobic molecule such as cholesterol, ergosterol, lithocholic acid, cholic acid, dinosterol, betuline, or oleanolic acid, which may be employed in order to retard the release rate of the agent from the copolymer coating. Such hydrophobic molecules prevent water penetration into the coating, but do not compromise the degradability of the coating. In addition, such molecules have melting points from 150° C. to 200° C. or decreases the coating diffusion coefficient for the biologically active agent, such as small drug molecule, to be released. Thus, such hydrophobic molecules provide for a more sustained release of a biologically active agent from the coating. The at least one hydrophobic molecule may be present in the coating in an amount of from about 0.1 wt. % to about 20 wt. %, preferably from 1.0 wt. % to 5.0 wt. %.

If it is desired to increase the hydrophilicity of the polymer, and thereby increase the degradation rate and drug releasing rate of the copolymer, the copolymer may be modified by partially replacing the aromatic moiety with an aliphatic moiety such as succinate and/or by replacing partially the alkylene with dioxyethylene. For example, terephthalate can be replaced by succinate in an amount of from about 0.1 mole % to about 20 mole %, preferably from about 0.1 mole % to about 5 mole %, by partially replacing dimethyl terephthalate as a starting component with dimethyl succinate. As another example, butylene is replaced with oxyethylene in an amount of from about 0.1 mole % to about 20 mole %, preferably from about 0.5 mole % to about 2 mole %, by replacing 1,4-butanediol with dimethyleneglycol as a starting component.

Examples of peptides or proteins which may advantageously be contained in the coating include, but are not limited to, immunogenic peptides or immunogenic proteins, which include, but are not limited to, the following:

Growth factors: bone morphogenetic proteins, transforming growth factors, fibroblast growth factors, epidermal growth factors, etc.

Toxins: diphtheria toxin, tetanus toxin

Viral surface antigens or parts of viruses: adenoviruses, Epstein-Barr Virus, Hepatitis A Virus, Hepatitis B Virus, Herpes viruses, HIV-1, HIV-2, HTLV-III, Influenza viruses, Japanese encephalitis virus, Measles virus, Papilloma viruses, Paramyxoviruses, Polio Virus, Rabies, Virus, Rubella Virus, Vaccinia (Smallpox) viruses, Yellow Fever Virus Bacterial surface antigens or parts of bacteria: *Bordetella pertussis, Helicobacter pylori, Clostridium tetani, Corynebacterium diphtheria, Escherichia coli, Haemophilus influenza, Klebsiella* species, *Legionella pneumophila, Mycobacterium bovis, Mycobacterium leprae, Mycrobacterium tuberculosis, Neisseria gonorrhoeae, Neisseria meningitidis, Proteus* species, *Pseudomonas aeruginosa, Salmonella* species, *Shigella* species, *Staphylococcus aureus, Streptococcus pyogenes, Vibrio cholera, Yersinia pestis*

Surface antigens of parasites causing disease or portions of parasites:

*Plasmodium vivax*—malaria, *Plasmodium falciparum*—malaria, *Plasmodium ovale*—malaria, *Plasmodium malariae*—malaria, *Leishmania tropica*—leishmaniasis, *Leishmania donovani*, leishmaniasis, *Leishmania branziliensis*—leishmaniasis, *Trypanosoma rhodescense*—sleeping sickness, *Trypanosoma gambiense*—sleeping sickness, *Trypanosoma cruzi*—Chagas' disease, *Schistosoma mansoni*—schistosomiasis, *Schistosomoma haematobium*—schistomiasis, *Schistosoma japonicum*—shichtomiasis, *Trichinella spiralis*—trichinosis, *Stronglyloides duodenale*—hookworm, *Ancyclostoma duodenale*—hookworm, *Necator americanus*—hookworm, *Wucheria bancrofti*—filariasis, *Brugia malaya*—filariasis, *Loa loa*—filariasis, *Dipetalonema perstaris*—filariasis, *Dracuncula medinensis*—filariasis, *Onchocerca volvulus*—filariasis Immunoglobulins: IgG, IgA, IgM, Antirabies immunoglobulin, Antivaccinia immunoglobulin Antitoxins: Botulinum antitoxin, diphtheria antitoxin, gas gangrene antitoxin, tetanus antitoxin.

Other peptides or proteins which may be encapsulated include, but are not limited to, antigens which elicit an immune response against Foot and Mouth Disease, hormones and growth factors such as follicle stimulating hormone, prolactin, angiogenin, epidermal growth factor, calcitonin, erythropoietin, thyrotropic releasing hormone, insulin, growth hormones, insulin-like growth factors 1 and 2, skeletal growth factor, human chorionic gonadotropin, luteinizing hormone, nerve growth factor, adrenocorticotropic hormone (ACTH), luteinizing hormone releasing hormone (LHRH), parathyroid hormone (PTH), thyrotropin releasing hormone (TRH), vasopressin, cholecystokinin, and corticotropin releasing hormone; cytokines, such as interferons, interleukins, colony stimulating factors, and tumor necrosis factors: fibrinolytic enzymes, such as urokinase, kidney plasminogen activator; and clotting factors, such as Protein C, Factor VIII, Factor IX, Factor VII and Antithrombin III. Examples of other proteins or peptides which may be encapsulated include, but are not limited to, albumin, atrial natriuretic factor, renin, superoxide dismutase, $\alpha_1$-antitrypsin, lung surfactant proteins, bacitracin, bestatin, cydosporine, delta sleep-inducing peptide (DSIP), endorphins, glucagon, gramicidin, melanocyte inhibiting factors, neurotensin, oxytocin, somostatin, terprotide, serum thymide factor, thymosin, DDAVP, dermorphin, Met-enkephalin, peptidoglycan, satietin, thymopentin, fibrin degradation product, des-enkephalin-α-endorphin, gonadotropin releasing hormone, leuprolide, α-MSH, and metkephamid. It is to be understood, however, that the scope of the present invention is not limited to any specific peptides or proteins.

Before applying the coating, the surface to which it is to be applied is preferably cleaned or treated to remove any contaminants and to promote good adhesion of the coating. Various methods for cleaning may be employed. The metallic implants may be rinsed with a degreaser, i.e. acetone, alkyl alcohols, etc. and then thoroughly rinsed with pure water.

In order to improve coating adhesion, various surface treatments may be applied to metal implants. Mechanical surface treatments, such as sand-blasting, scoring, polishing and grinding can increase surface roughness of the implants and improve the bonding strength between the coatings and metal substrate. For similar purposes, chemical surface treatments may be also applied to metal substrates prior to coating. Among others chemical treatments available for metals, acid etchings will be preferred by treating implantable devices with strong mineral acids, such as hydrofluoric, hydrochloric, sulfuric, nitric and perchloric acids. It may also useful to treat the metal devices with oxidising agents such as nitric acid, peroxyhalogen acids, hydroxyperoxides, or hydrogen peroxide to form a fresh metal oxide layer. After the mechanical or chemical treatment, it is necessary to rinse the implants with pure water under ultrasound for removal of surface contaminants.

A coating according to the invention may be applied to a surface by methods known to those skilled in the art, like by brushing, spraying, wiping, dipping, extruding or injecting. The latter three methods are preferred when porous structures or fibrous meshes are to be coated. Use of these methods allows penetration of the copolymer of which the coating is formed inside the pores of the devices and a (uniform) coating of the total surface area. Brushing and spraying are preferred in case of non-porous devices.

If desired, organic solvents may be used to dissolve the copolymer. Suitable solvents are chloroform, dichloromethane, N-methyl-2-pyrrolidone, dimethyl sulfoxide, acetone, hexafluoroisopropanol and the like. The selection of a suitable solvent will be dependent on the composition of the chosen copolymer. Alternatively, heat may be applied to process a copolymer of which a coating is to be formed.

A biologically active agent may be incorporated into the coating by dissolving it in the copolymer solution of which the coating is formed. Hence, a homogeneous solution is formed or a suspension is formed by dispersion. Alternatively, a solution of a biologically active agent may be mixed with the copolymer solution to form a homogeneous mixture, or an emulsion. Also, a biologically agent can be incorporated by physically mixing with the copolymer, for example by extrusion. Since in the latter case heat is applied, care must be taken not to harm the stability and/or activity of the biologically active agent.

If it is desired that a porous coating is formed, a pore-forming agent can be included in the solution or suspension of the copolymer from which the coating is formed. Pore-forming agents may include organic solvents, water, salts (sodium chloride, sodium citrate, and the like), sugars and water-soluble synthetic polymers. Using such pore-forming agents, pores can be created by leaching-out of the agent, or by phase separation.

The thickness of the coatings of this invention may range from a few microns up to any desired thickness (up to a few hundred microns). The thickness of the coating may be adjusted by the viscosity of the copolymer solution that is used to prepare the coating. The viscosity of the copolymer solution may be adjusted by parameters like the molecular weight of the copolymer, the copolymer concentration in the solution, the selected solvent, the temperature, etc. In case of spraying or brushing, spraying time and flow rate may also influence the thickness of the coating.

The invention will be further elucidated by the following, non-restrictive example.

EXAMPLE

A porous scaffold was produced as described in example 1 of European patent application 01200328.1, the contents of which are incorporated herein by reference, from a copolymer of polyethylene glycol (PEG, MW=300 g/mole) and polybutylene terephthalate (PBT), wherein the weight percentage PBT was 55%. The porosity of the scaffold was approximately 77 v/v %. About 400 mg of the scaffold to be coated was placed on a grid that was connected to a vacuum pump (see FIG. 1 for a schematic representation).

The coating emulsion was prepared by mixing a protein solution (1.0 ml, 50 mg lysozyme per ml phosphate buffered saline (PBS), pH 7.4) with a polymer solution (6 ml chloroform, Ig copolymer of polyethylene glycol (PEG, MW=1000 g/mole) and polybutylene terephthalate (PBT), wherein the weight percentage PBT was 30%.) using ultra-turrax mixing (30 s at 19 krpm, Ika Labortechnik T25). The resulting water-in-oil emulsion was poured on top of the scaffold, and a vacuum of 300 Torr was applied for 5 minutes. Thereafter, the scaffolds were dried overnight under vacuum at room temperature.

To evaluate the release of lysozyme form the coated scaffolds, pieces of approximately 75 mg were incubated in 1 ml PBS (pH 7.4). Vials were continuously shaken at 37° C. and samples were taken at various time points. The protein concentration in the buffer solution was determined using a standard Coomassie Blue assay (Pierce). In FIG. 2, the release of lysozyme from the coated scaffolds is presented.

The invention claimed is:

1. A medical device comprising a surface and a coating applied to the surface of the medical device,
    the coating comprising a copolymer of a polyalkylene glycol terephthalate and an aromatic polyester, with the copolymer having a weight average molecular weight between about 10,000 and about 300,000,
    the coating further comprising a biologically active agent,
    and the surface being a material selected from the group consisting of metals, metal alloys, ceramics, and glasses.

2. A medical device according to claim 1, wherein the polyalkylene glycol is selected from the group consisting of polyethylene glycol terephthalate, polypropylene glycol terephthalate, and polybutylene glycol terephthalate.

3. A medical device according to claim 2, wherein the polyalkylene glycol is polyethylene glycol terephthalate.

4. A medical device according to claim 1, wherein the polyester is selected from the group consisting of polyethylene terephthalate, polypropylene terephthalate, and polybutylene terephthalate.

5. A medical device according to claim 4, wherein the polyester is polybutylene terephthalate.

6. A medical device according to claim 1, wherein the copolymer comprises 20–90 wt. %, based on the weight of the copolymer, of the polyalkylene glycol.

7. A medical device according to claim 1, wherein the weight average molecular weight of the polyalkylene glycol is from about 150 to about 4000.

8. A medical device according to claim 1, wherein the biologically active agent is chosen from the group consisting of antimicrobial agents, antibacterial agents, anti-fungal agents, anti-viral agents, anti-tumor agents, immunogenic agents, lipids, lipopolysaccharides, hormones and growth factors.

9. A medical device according to claim 1, wherein the biologically active agent is chosen from the group consisting of peptides, oligopeptides, polypeptides and proteins.

10. A medical device according to claim 1, wherein the surface is a surface of a medical device selected from the group consisting of catheters, stents, fibres, non-woven fabrics, vascular grafts, porous metals for acetabulum revision, and porous scaffolds for tissue engineering.

11. A medical device according to claim 1 which is porous upon application to the surface.

12. A method for applying the coating to the surface of the medical device according to claim 1, comprising brushing, spraying, wiping, dipping, extruding or injecting.

13. A method according to claim 12, wherein the surface is cleaned and/or subjected to a mechanical treatment prior to application of the coating.

14. A method according to claim 12, wherein the coating is applied from a solution or suspension of the copolymer and the biologically active agent.

15. A method according to claim 14, wherein a pore-forming agent is included in the solution or suspension.

16. A medical device according to claim 1 selected from the group consisting of catheters, fibres, non-woven fabrics, vascular grafts, porous metals for acetabulum revision, dental filling materials, materials used in osteo-synthesis, cardiac patches, sutures, soft and hard tissue scaffolds and fillers, stents, bone void fillers intended for the repair of bone defects, intrauterine devices, root canal fillers, drug delivery pumps, implantable infusion pumps, spacer devices, implants containing medicinal products, and scaffolds for tissue engineering.

17. A medical device according to claim 1, wherein the copolymer comprises 40–70 wt. %, based on the weight of the copolymer, of the polyalkylene glycol.

18. A medical device according to claim 1, wherein the weight average molecular weight of the polyalkylene glycol is from about 200 to about 1500.

19. A medical device according to claim 1, wherein the weight average molecular weight of the copolymer lies between about 40,000 and about 120,000.

20. A medical device according to claim 16, wherein the material used in osteo-synthesis is a pin or a bone screw.

21. A medical device according to claim 16, wherein the hard tissue scaffold and filler is calcium phosphate or bioglass.

* * * * *